United States Patent [19]
Hirooka et al.

[11] Patent Number: 5,097,838
[45] Date of Patent: Mar. 24, 1992

[54] ULTRASONIC ENDOSCOPE

[75] Inventors: Kenji Hirooka, Hachioji; Yoshitake Saito, Kunitachi; Takeshi Yokoi, Fuchu; Yoshihito Shimizu, Sagamihara, all of Japan

[73] Assignee: Olympus Optical Co., Ltd., Tokyo, Japan

[21] Appl. No.: 464,963

[22] Filed: Jan. 16, 1990

[30] Foreign Application Priority Data

Apr. 27, 1989 [JP] Japan ................... 1-108784
Apr. 27, 1989 [JP] Japan ................... 1-108787

[51] Int. Cl.⁵ .................................. A61B 8/12
[52] U.S. Cl. ............................ 128/662.06; 128/4
[58] Field of Search ............. 128/662.006, 661.003, 128/662.003, 4-9, 662.06, 662.03, 661.03, 661.04, 661.05, 661.06

[56] References Cited

U.S. PATENT DOCUMENTS

| | | | |
|---|---|---|---|
| 3,779,234 | 12/1973 | Eggleton et al. | 128/662.006 |
| 4,374,525 | 2/1983 | Baba | 128/662.06 |
| 4,433,692 | 2/1984 | Baba | 128/662.06 |
| 4,779,624 | 10/1988 | Yokoi | 128/660.03 |
| 4,807,634 | 2/1989 | Enjoji et al. | 128/660.01 |

FOREIGN PATENT DOCUMENTS

| | | | |
|---|---|---|---|
| 88620 | 9/1983 | European Pat. Off. | 128/662.06 |
| 60-227740 | 1/1985 | Japan . | |
| 61-57908 | 4/1986 | Japan . | |

*Primary Examiner*—Kyle L. Howell
*Assistant Examiner*—Kevin Pontius
*Attorney, Agent, or Firm*—Frishauf, Holtz, Goodman & Woodward

[57] ABSTRACT

An ultrasonic endoscope comprises an insertion section having a distal end portion and a proximal end portion, an ultrasonic probe disposed in the distal end portion of the insertion section and adapted to generate ultrasonic oscillations and detect reflected waves, an operating section connected to the proximal end portion of the insertion section and used to bend the insertion section, and an auxiliary operating section connected to the rear end of the operating section, the auxiliary operating section including a rotation drive unit for rotating the ultrasonic probe.

5 Claims, 23 Drawing Sheets

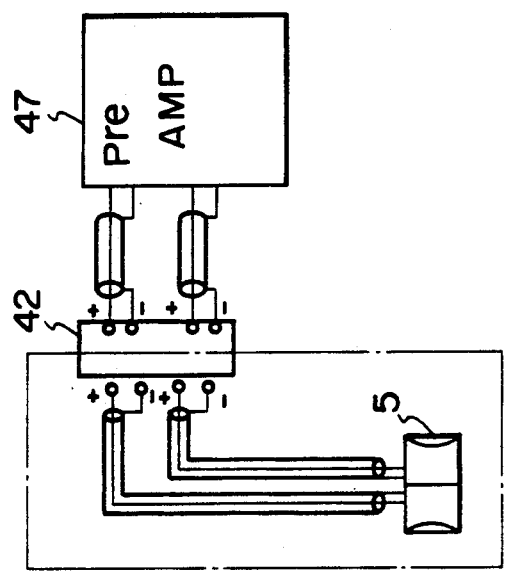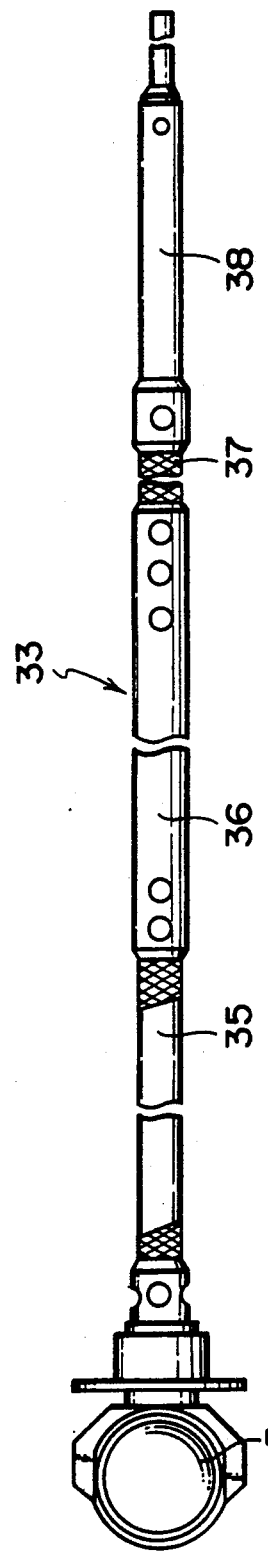

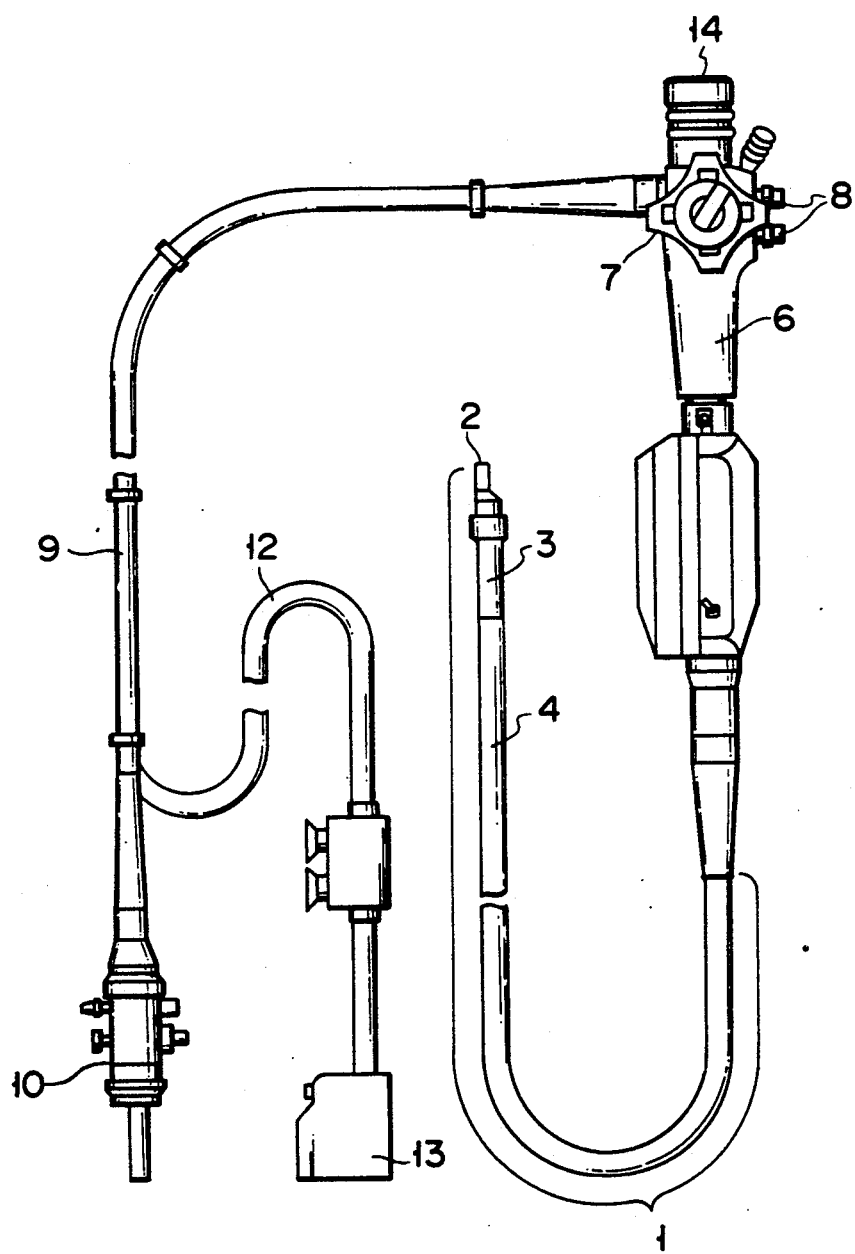
F I G. 20

ULTRASONIC ENDOSCOPE

BACKGROUND OF THE INVENTION

1. Field of the Invention

The present invention relates to an ultrasonic endoscope having having an ultrasonic probe for generating ultrasonic oscillations and detecting resulting reflected waves.

2. Description of the Related Art

Recently, there have been developed ultrasonic endoscopes in which an ultrasonic transmitter-receiver (ultrasonic probe) is attached to the distal end of an insertion section of the endoscope, in order to facilitate close examination of internal organs in the depths of the human body through the body cavity.

The ultrasonic endoscopes may be roughly classified into two types, mechanical and electronic ultrasonic scanning types. Among the endoscopes of the mechanical scanning type, radial-scanning endoscopes, in which an ultrasonic transmitter-receiver is rotated around the central axis of the insertion section, is adapted for ultrasonic diagnosis through the lumina, such as the alimentary canals.

Typical radial-scanning ultrasonic endoscopes are disclosed in Published Unexamined Japanese Patent Application No. 60-227740 or Published Unexamined Japanese Utility Model Application No. 61-57908, for example. In these ultrasonic endoscopes, an ultrasonic transmitter-receiver attached to the distal end of an insertion section of the endoscope is rotated by means of a motor through the medium of a hollow drive shaft. A signal from the transmitter-receiver is fetched from a rotary signal transmission unit at the proximal end portion of the drive shaft, through a signal cable passed through the hollow portion of the shaft. The motor and the signal transmission unit are housed in an auxiliary operating section, which is disposed between the insertion section and an operating section of the endoscope.

If the auxiliary operating section is interposed in this manner, however, the distance between the respective grip portions of the insertion section and the operating section is too great for an operator to hold the two grip portions at the same time, so that the operating efficiency is lowered.

SUMMARY OF THE INVENTION

An object of the present invention is to provide an ultrasonic endoscope with high operating efficiency.

Another object of the invention is to provide an ultrasonic endoscope having an auxiliary operating section behind an operating section.

The above objects are achieved by an ultrasonic endoscope constructed as follows. The ultrasonic endoscope comprises an insertion section having a distal end portion and a proximal end portion, an ultrasonic probe disposed in the distal end portion of the insertion section and adapted to generate ultrasonic oscillations and detect reflected waves, an operating section connected to the proximal end portion of the insertion section and used to bend the insertion section, and an auxiliary operating section connected to the rear end of the operating section, the auxiliary operating section including a rotation drive unit for rotating the ultrasonic probe.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 9 is a diagram illustrating the connection between an ultrasonic probe and an amplifier;

FIG. 10 is a plan view of a probe shaft;

FIG. 20 is a side view of an ultrasonic endoscope according to a second embodiment of the present invention;

DETAILED DESCRIPTION OF THE PREFERRED EMBODIMENT

Preferred embodiments of the present invention will now be described in detail with reference to the accompanying drawings.

Figure 1:
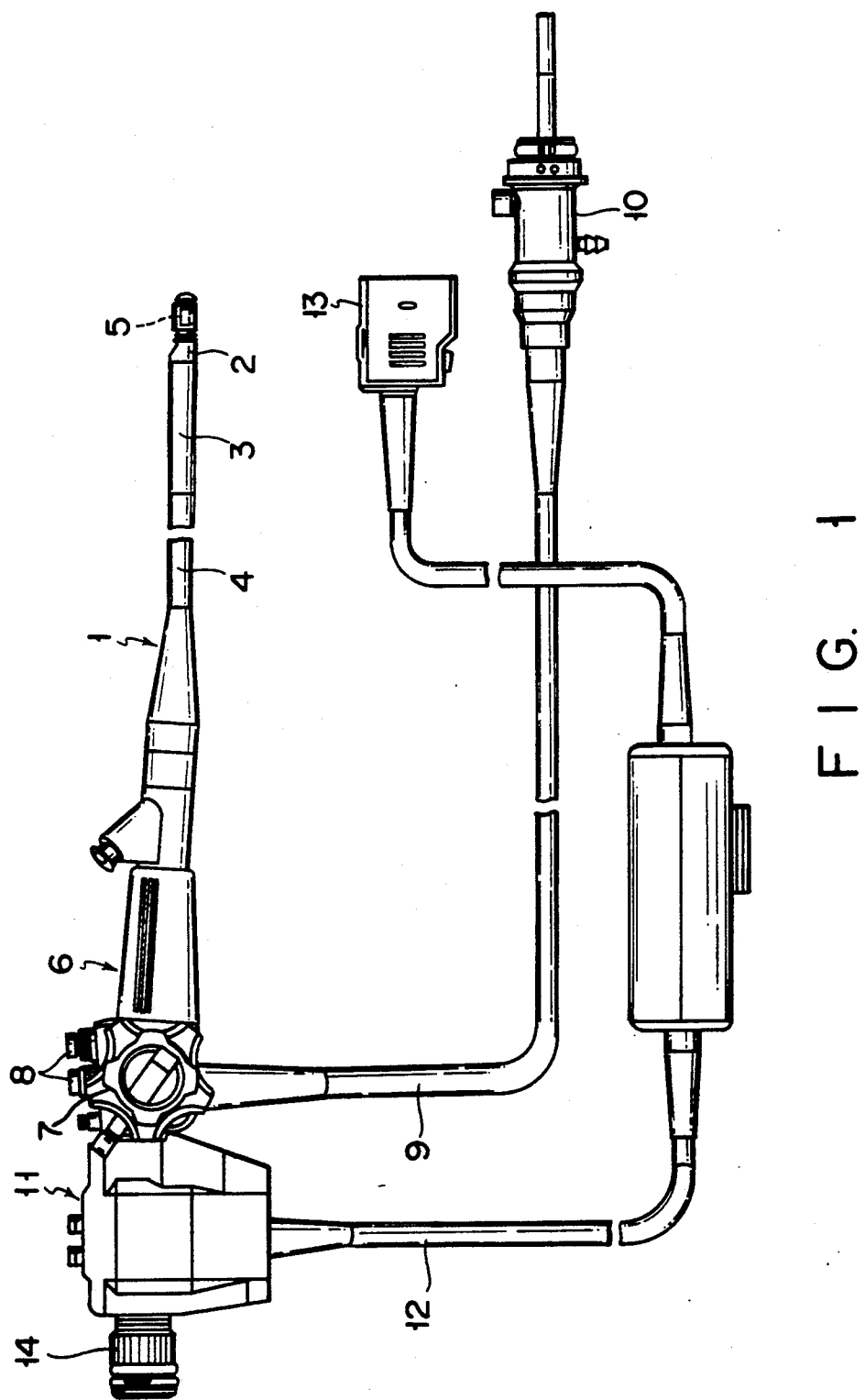
FIG. 1 is a side view of an ultrasonic endoscope according to a first embodiment of the present invention.
Figure 2:
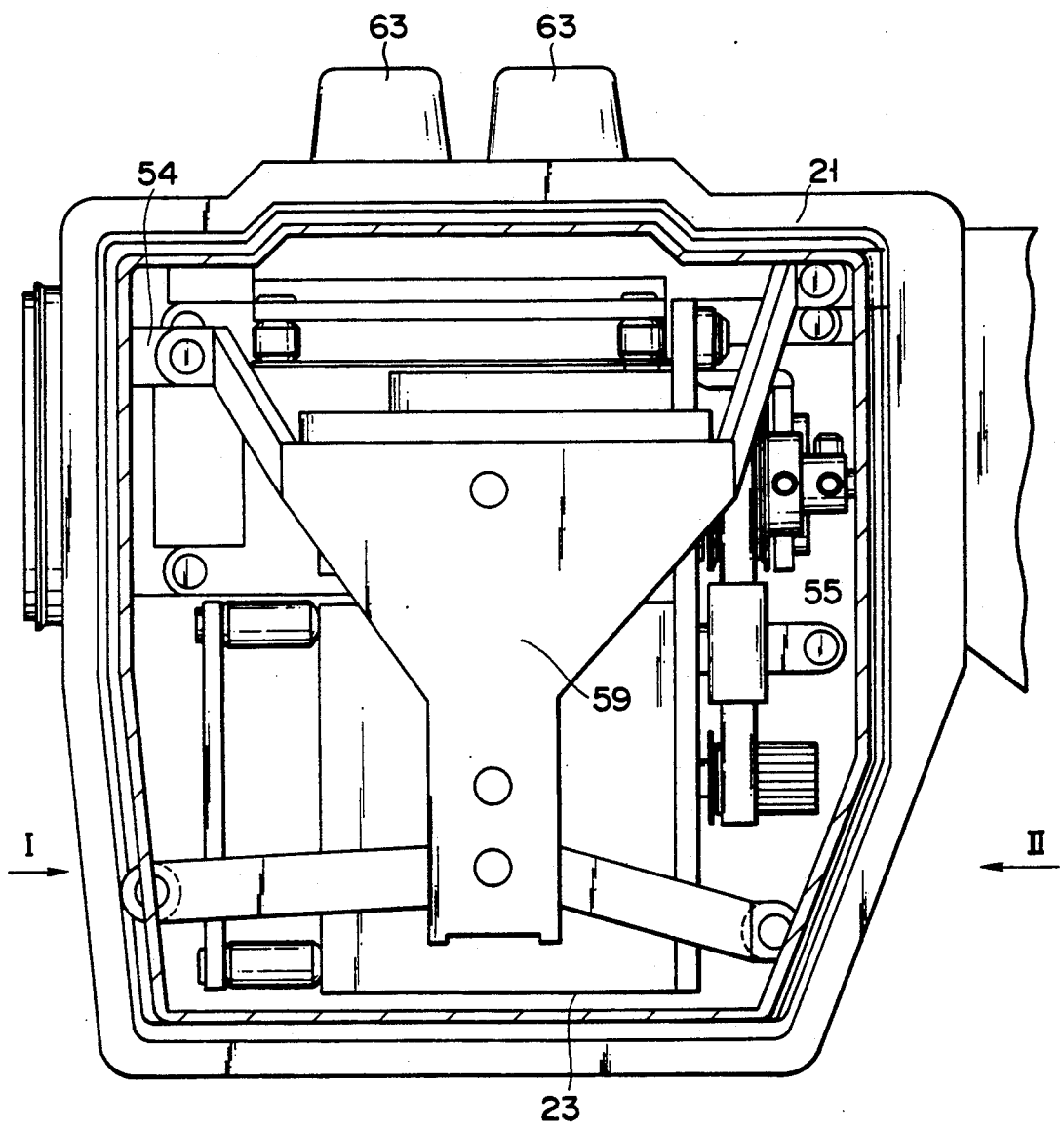
FIG. 2 is a side view, partially in section, showing the front side of an auxiliary operating section of the ultrasonic endoscope.

FIG. 1 shows an outline of an ultrasonic endoscope according to a first embodiment of the invention. In FIG. 1, numeral 1 denotes an insertion section of the endoscope, which comprises distal end portion 2, bending portion 3, and flexible portion 4. Ultrasonic probe 5, used to generate ultrasonic oscillations and detect reflected waves, is provided at the distal end of insertion section 1. Numeral 6 denotes an operating section of the endoscope attached to the rear end of insertion section 1. Operating section 6 is provided with bending control knob 7 for controlling bending portion 3 and air/water feed buttons 8, and is connected with universal cord 9. First connector 10, which is adapted to be connected to a light source unit (not shown), is attached to the distal end of cord 9.

An auxiliary operating section 11 for controlling ultrasonic probe 5 is attached to the rear end of operating section 6. Electric cable cord 12 is connected to section 11, and second connector 13, which is adapted to be connected to an ultrasonic observation device (not shown), is attached to the distal end of cord 12. Numeral 14 denotes an eyepiece portion which is attached to the rear end of auxiliary operating section 11. Eyepiece portion 14 is situated behind the center of gravity of operating section 6.

Figure 3:
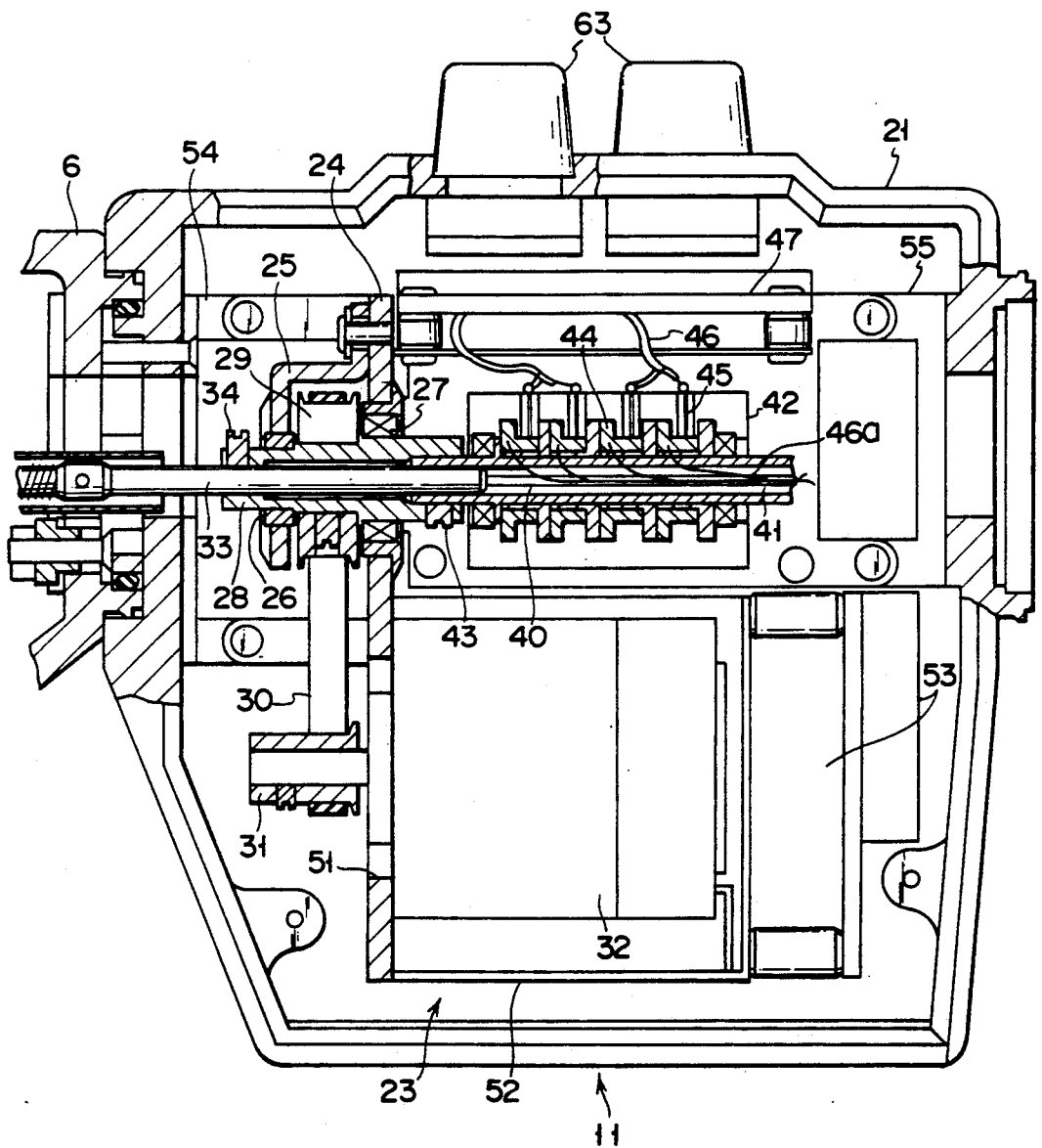
FIG. 3 is a side view, partially in section, showing the rear side of the auxiliary operating section.

FIGS. 2 to 8 show the details of auxiliary operating section 11. In FIGS. 2 to 8, numerals 21 and 22 denote an auxiliary operating section housing and an auxiliary operating section cover, respectively. Housing 21 contains drive unit 23 which is used to rotate ultrasonic probe 5 around the axis of insertion section 1. As shown in FIG. 3, unit 23 includes base 24, shaft holder 25 mounted on base 24, hollow drive shaft 28 rotatably supported on holder 25 by means of bearings 26 and 27, and motor 32 which drives shaft 28 through the medium of first pulley 29, belt 30, and second pulley 31. The rear end portion of probe shaft 33 is inserted in a hole of drive shaft 28, and is fixed by means of screw 34. Ultrasonic probe 5 is attached to the front end of shaft 33, so that the rotation of motor 32 is transmitted through shaft 33 to probe 5.

In probe shaft 33, as shown in FIG. 10, first flexible shaft 35, seal shaft 36, second flexible shaft 37, and fixed shaft 38 are connected in succession. As shown in FIG. 11, shaft 33 is guided into auxiliary operating section 11 by means of guide tubes 39a and 39b, which are arranged in insertion section 1 and operating section 6, respectively. Probe shaft 33 is hollow, and its hollow portion is penetrated by first signal cable 40 which is connected to ultrasonic probe 5.

Rotary signal transmission unit 42 having axial through hole 41 is attached to the rear end of drive shaft 28, and is fixed by means of screw 43. Unit 42 includes slip rings 44, which are rotatable integrally with shaft 28, and brushes 45 in contact with rings 44. Each ring 44 is connected with one end of first signal cable 40, while each brush 45 is connected with one end of second signal cable 46 which is connected to amplifier 47. Thus, a signal from ultrasonic probe 5 is transferred through signal transmission unit 42 to amplifier, as shown in FIG. 9.

Figure 4:
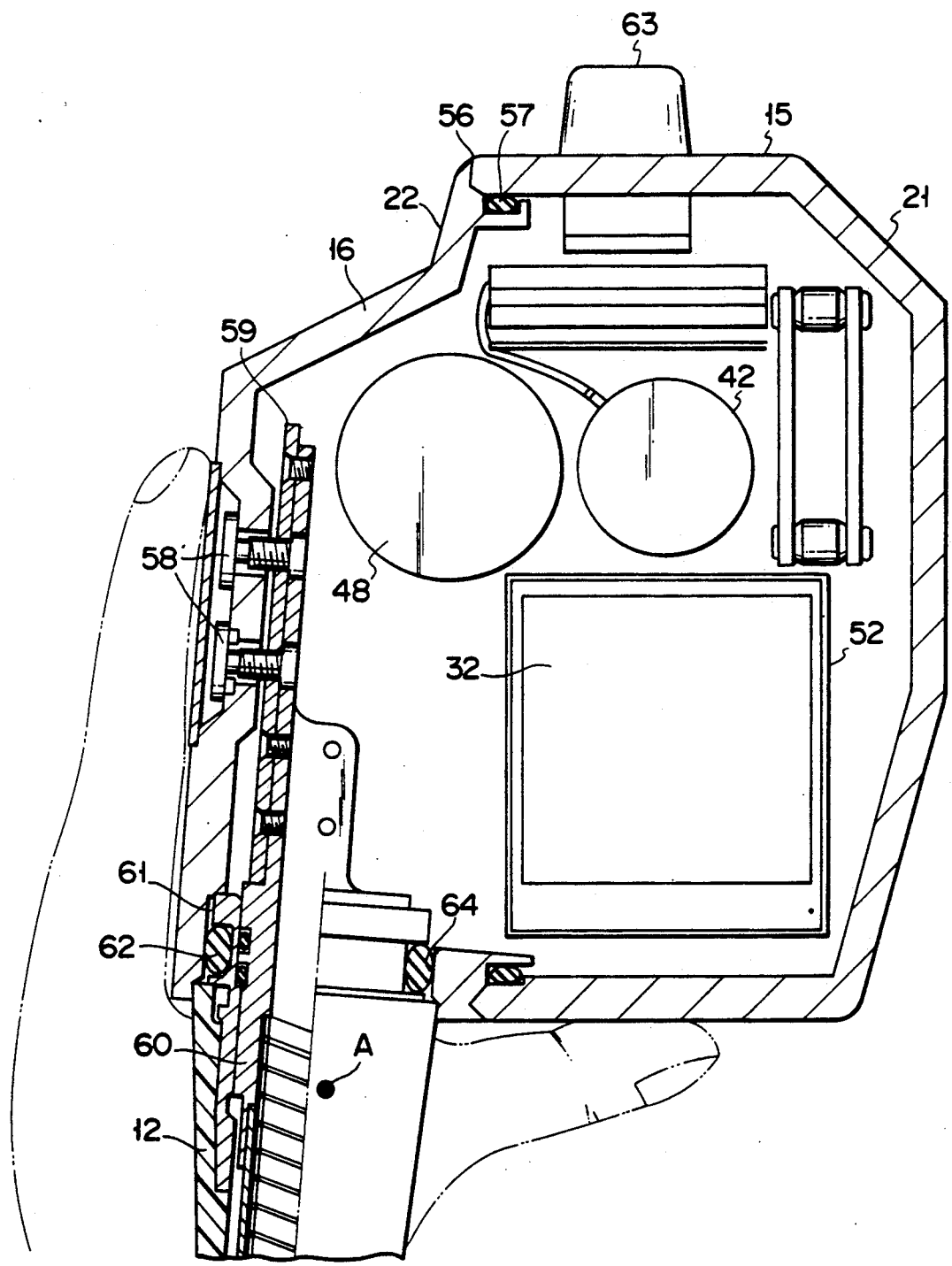
FIG. 4 is a sectional view of the interior of the auxiliary operating section, taken in the direction of arrow I of FIG. 2.

As shown in FIG. 4, numeral 48 denotes an encoder for detecting the rotational position of ultrasonic probe 5. The rotation of motor 32 is transmitted to encoder 48 through second pulley 31, belt 30, and third pulley 49. Idler 50 is disposed between second and third pulleys 31 and 49, whereby a suitable tension is applied to belt 30. The ratio between the respective numbers of teeth of pulleys 29, 31 and 49 is set to 2:1:2.

Figure 5:
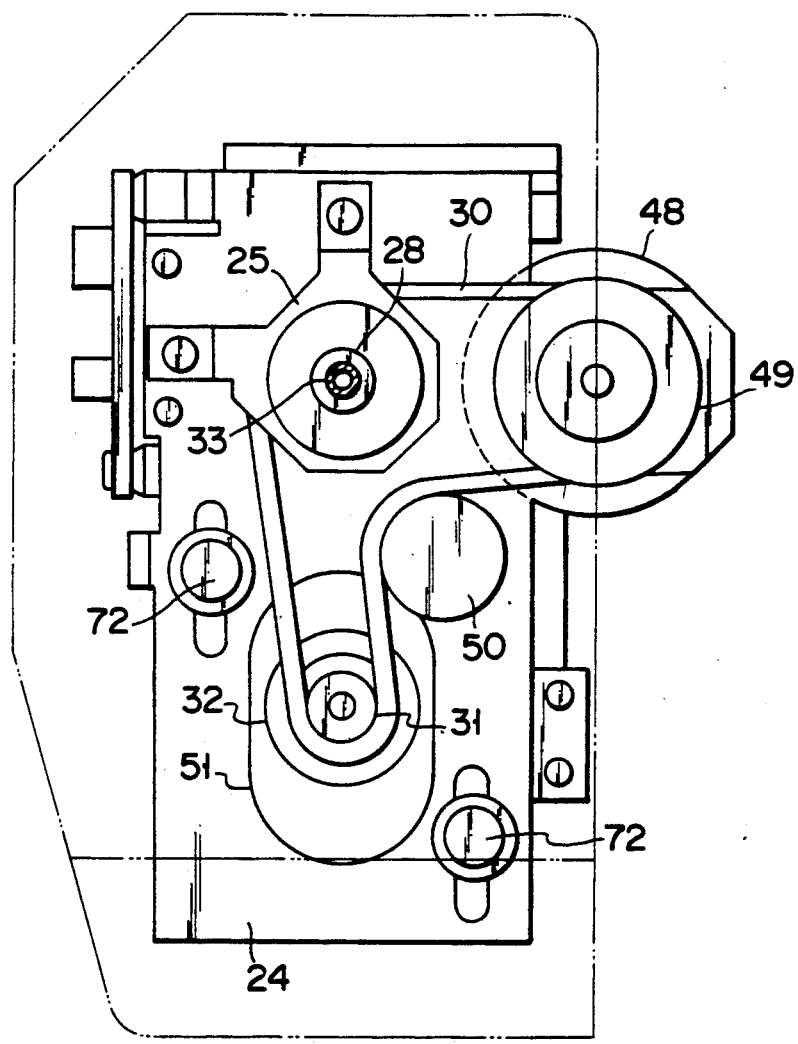
FIG. 5 is a schematic view of the interior of the auxiliary operating section, taken in the direction of arrow II of FIG. 2.
Figure 6:
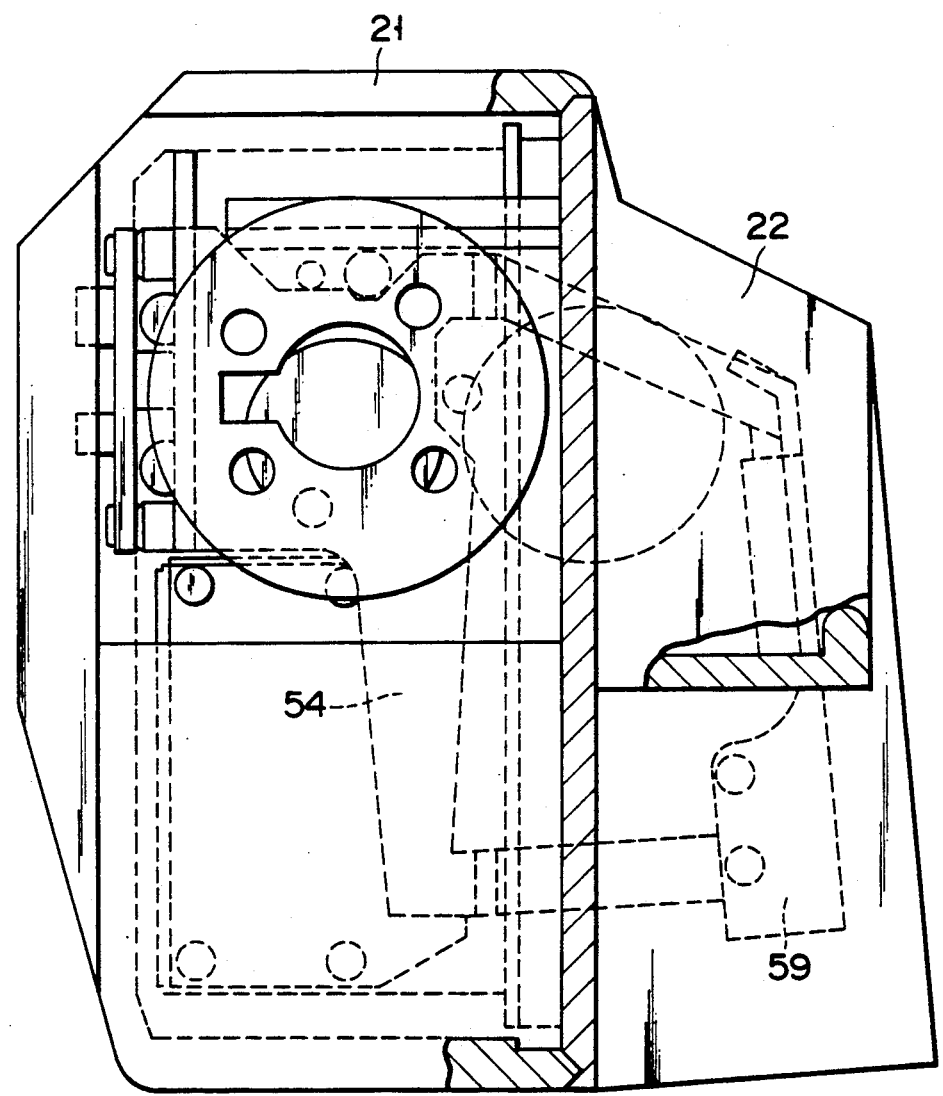
FIG. 6 is a cutaway view of the interior of the auxiliary operating section, taken in the direction of arrow II of FIG. 2.
Figure 7:
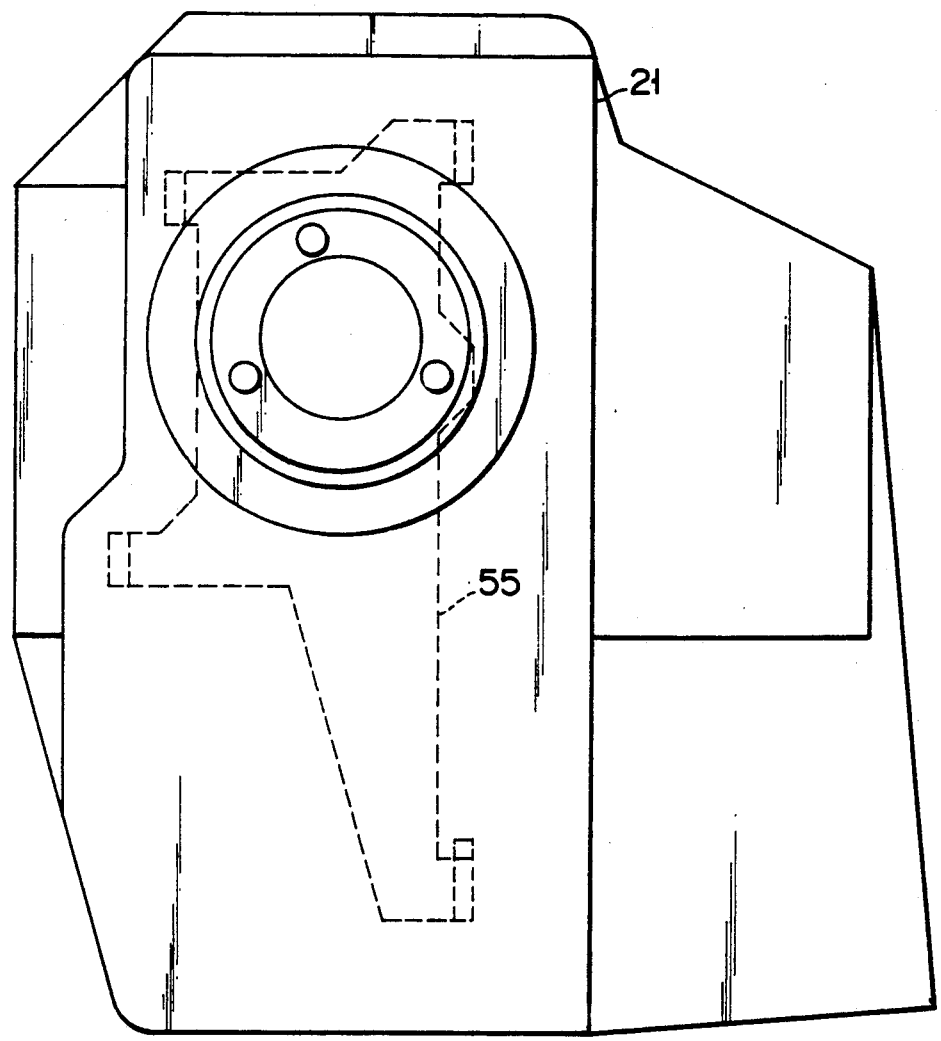
FIG. 7 is a front view of the interior of the auxiliary operating section, taken in the direction of arrow II of FIG. 2.
Figure 8:
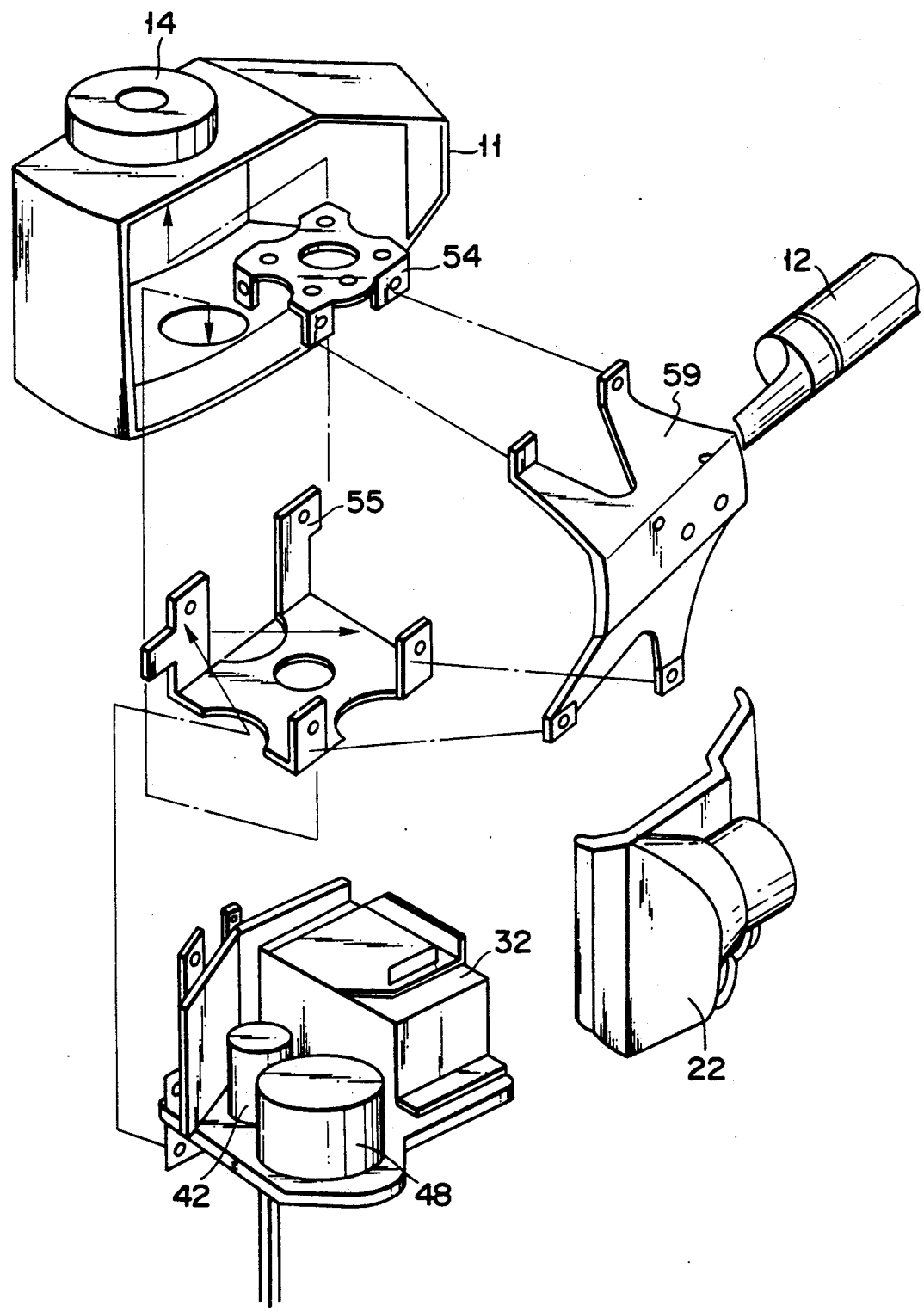
FIG. 8 is an exploded perspective view showing components of the auxiliary operating section.

Motor 32 is situated above supporting point A, at which operating section 6 is supported in hand, as shown in FIG. 4, and is fixed to base 24 by means of screw 72, as shown in FIG. 5. The drive shaft of motor 32 extends forward through oblong hole 51 in base 24. As shown in FIG. 3, moreover, shield plate 52 surrounds motor 32, and noise filters 53 are provided on plate 52. Drive unit 23 is connectedly fixed by means of tractor members 54 and 55 arranged at the front and rear portions, respectively, of auxiliary operating section housing 21.

As shown in FIG. 4, auxiliary operating section cover 22 is fitted on V-shaped edge 56 at the open edge portion of auxiliary operating section housing 21 with gasket 57 between them. Cover 22 is fixed to metal fitting 59 on tractor members 54 and 55 by means of fixing screws 58. Electric cable cord 12, which is passed through hole portion 64 in cover 22, is fixed to fitting 59 by means of ferrule 60, and auxiliary operating section cover 22 and cord 12 are fixed to each other by means of retainer 61 attached to ferrule 60 and gasket 62.

Auxiliary operating section housing 21 is provided with switch 63 for controlling the ultrasonic function. Switch 63 has a switching function to freeze an ultrasonic picture by previously setting the ultrasonic observation device (not shown), a release function to record the frozen ultrasonic picture, and a function to animate the picture and cause a recording device to store it.

Figure 11A:
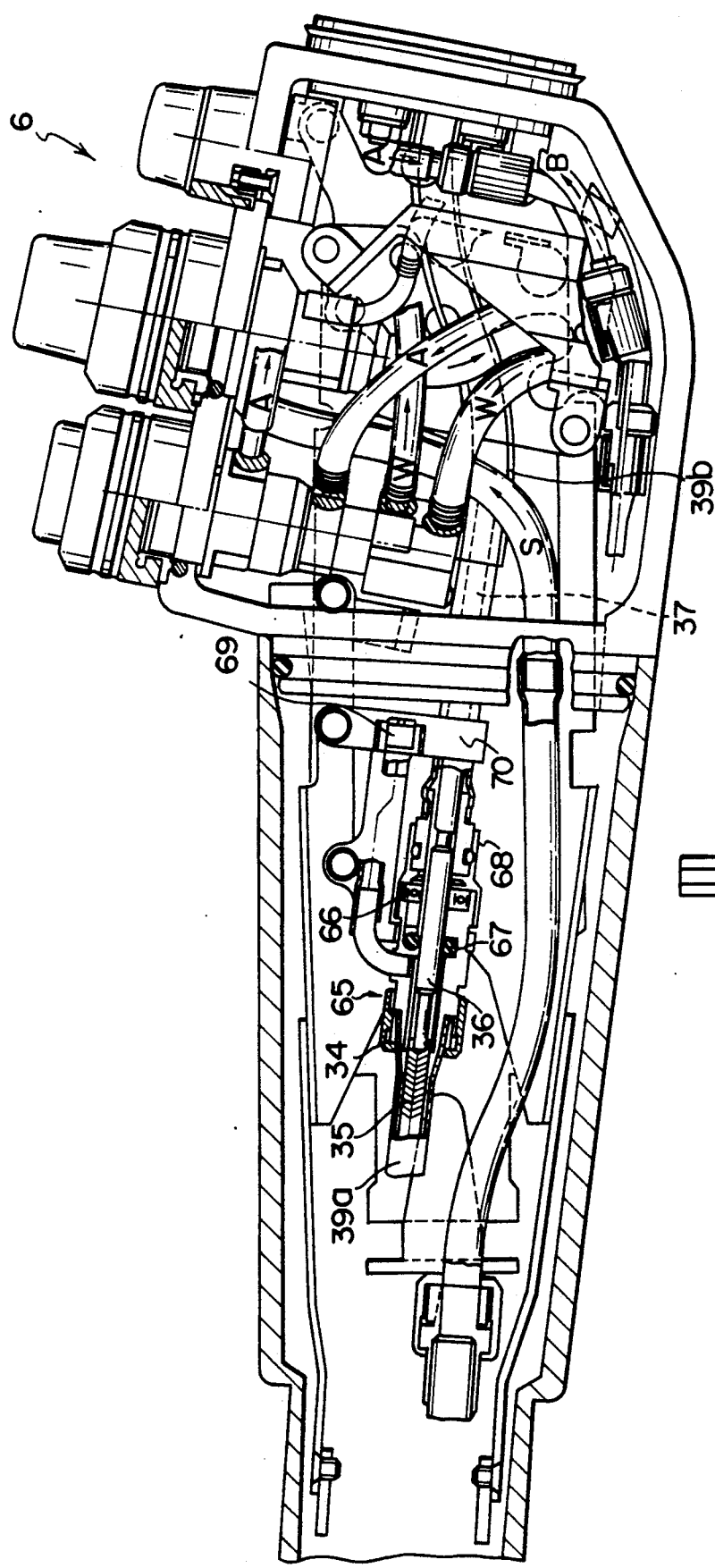
FIG. 11A is a side view, partially in section, showing an operating section of the endoscope.
Figure 11C:
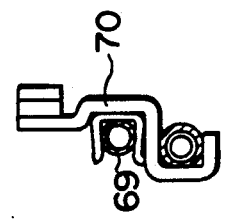
FIG. 11C is a partial view of a mouthpiece removably mounted on a retainer.
Figure 11B:
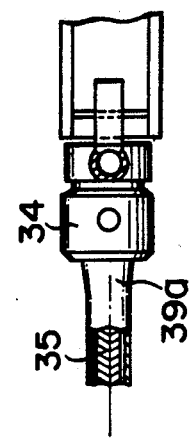
FIG. 11B is a partial view showing a connecting portion of a guide tube.

FIG. 11A shows the interior of operating section 6, in which is provided seal portion 65 for sealing an ultrasonic transmission medium into guide tube 39a. Portion 65, which is composed of bearing 66, seal member 67, and housing 68, seals the outer periphery of seal shaft 36. The side face of housing 68 has a hole communicating with the interior of tube 39a, and is fitted with mouthpiece 69 through which the ultrasonic transmission medium is sealed into tube 39a. Mouthpiece 69 is removably mounted on retainer 70 as shown in FIG. 11C. Guide tube 39a is connected to the front end portion of housing 68 by nut 34 as shown in FIG. 11B.

Inside operating section 6, second flexible shaft 37 of probe shaft 33 meanders through guide tube 39b to be guided thereby into auxiliary operating section 11. Guide tube 39b has a double-tube structure, and its inner tube is connectedly fixed to housing 68 of seal portion 65, while its outer tube is connectedly fixed to the junction of operating section 6 and auxiliary operating section 11.

In the ultrasonic endoscope according to the first embodiment, rotary signal transmission unit 42 is axially penetrated by through hole 41 which communicates with the hollow portion of probe shaft 33. Accordingly, first signal cable 40 connected to ultrasonic probe 5 and third signal cables 46a connected to slip rings 44 of transmission unit 42 can be easily connected to each other at the rear end portion of unit 42 in through hole 41. Thus, no special space is required for the connection, so that auxiliary operating section 11 can be reduced in size. Since the rear end portion of probe shaft 33 is fixedly fitted in the hollow portion of drive shaft 28, moreover, variation of the length of shaft 33 can be absorbed by the connection between the hollow portion of shaft 28 and the penetrated portion of rotary signal transmission unit 42. Furthermore, motor 32 is situated close to supporting point A of the grip portion, as shown in FIG. 4, so that auxiliary operating section can be held with good balance, and the operating efficiency can be improved.

Figure 12B:
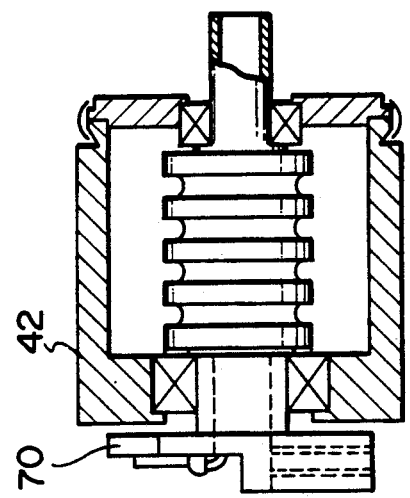
FIGS. 12A and 12B are a front view and a side view, respectively, showing a modification of a rotary signal transmission unit.
Figure 12A:
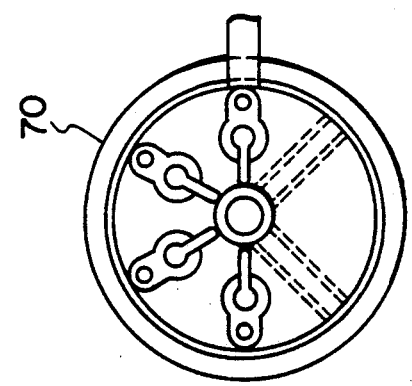

Preferably, base plate 70 is disposed at the junction of rotary signal transmission unit 42 and the signal cable, as shown in FIGS. 12A and 12B.

Figures 13A, 13B:
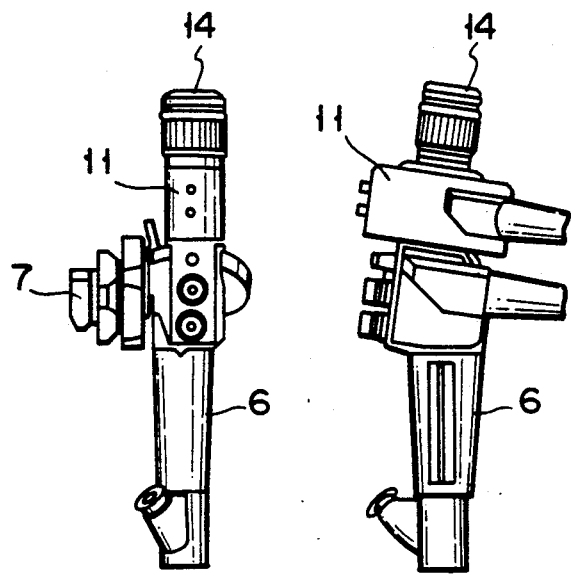
FIGS. 13A and 13B are a plan view and a side view, respectively, showing an endoscope operating section and an auxiliary operating section according to a first modification of the first embodiment.
Figure 14:
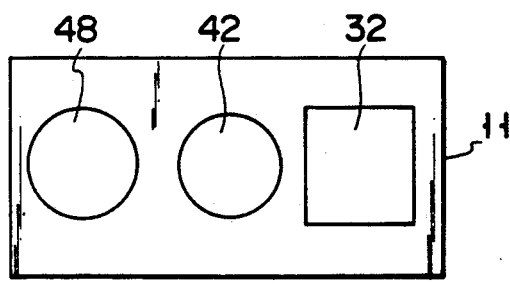
FIG. 14 is a diagram showing a layout of the interior of the auxiliary operating section according to the first modification.

FIGS. 13A, 13B and 14 show a first modification of ultrasonic endoscope according to the first embodiment. Inside auxiliary operating section 11, in this modification, motor 32, rotary signal transmission unit 42, and encoder 48 are arranged in series on the same plane.

Figures 15A, 15B:
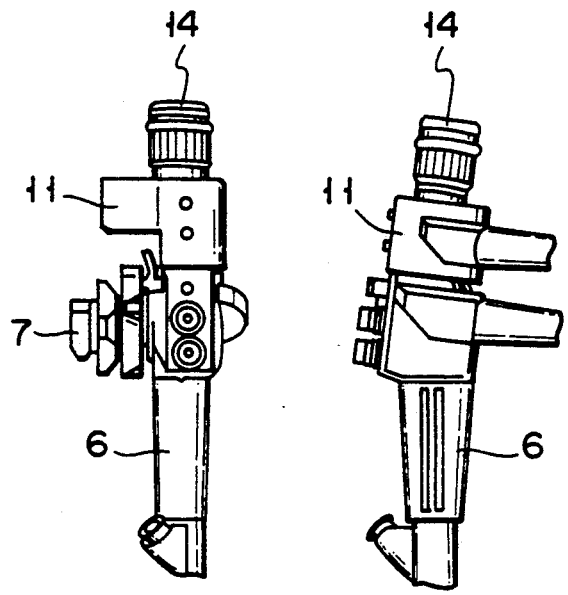
FIGS. 15A and 15B are a plan view and a side view, respectively, showing an endoscope operating section and an auxiliary operating section according to a second modification of the first embodiment.
Figure 16:
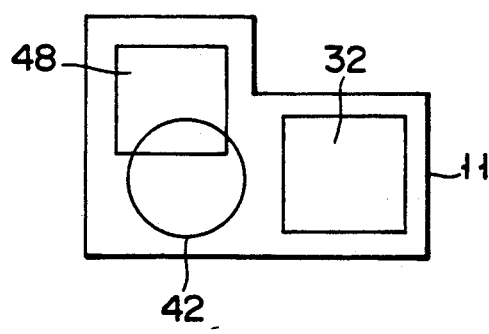
FIG. 16 is a diagram showing a layout of the interior of the auxiliary operating section according to the second modification.

FIGS. 15A, 15B and 16 show a second modification, in which motor 32 and rotary signal transmission unit 42 are arranged in series on the same plane, while encoder 48 is located by the side of unit 42.

Figures 17A, 17B:
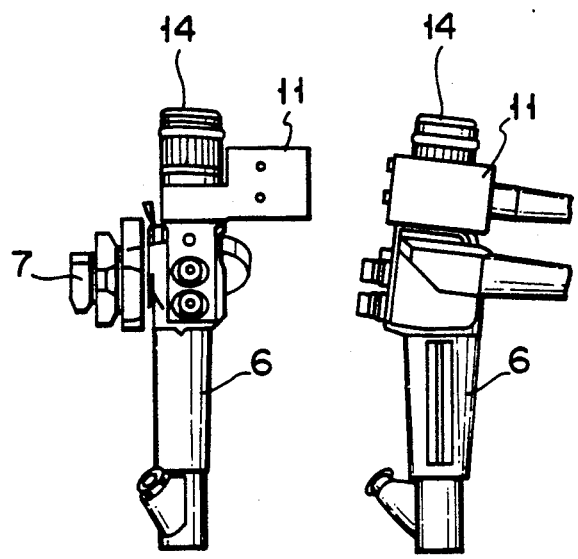
FIGS. 17A and 17B are a plan view and a side view, respectively, showing an endoscope operating section and an auxiliary operating section according to a third modification of the first embodiment.
Figure 18:
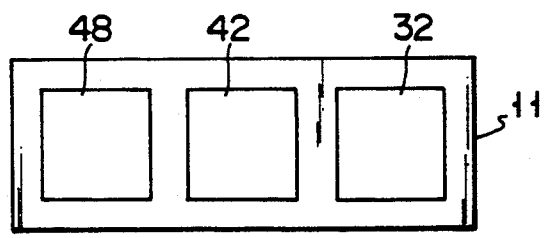
FIG. 18 is a diagram showing a layout of the interior of the auxiliary operating section according to the third modification.

FIGS. 17A, 17B and 18 show a third modification, in which motor 32, rotary signal transmission unit 42, and encoder 48 are arranged in series on the same plane, as in the case of the first modification.

Figure 19:
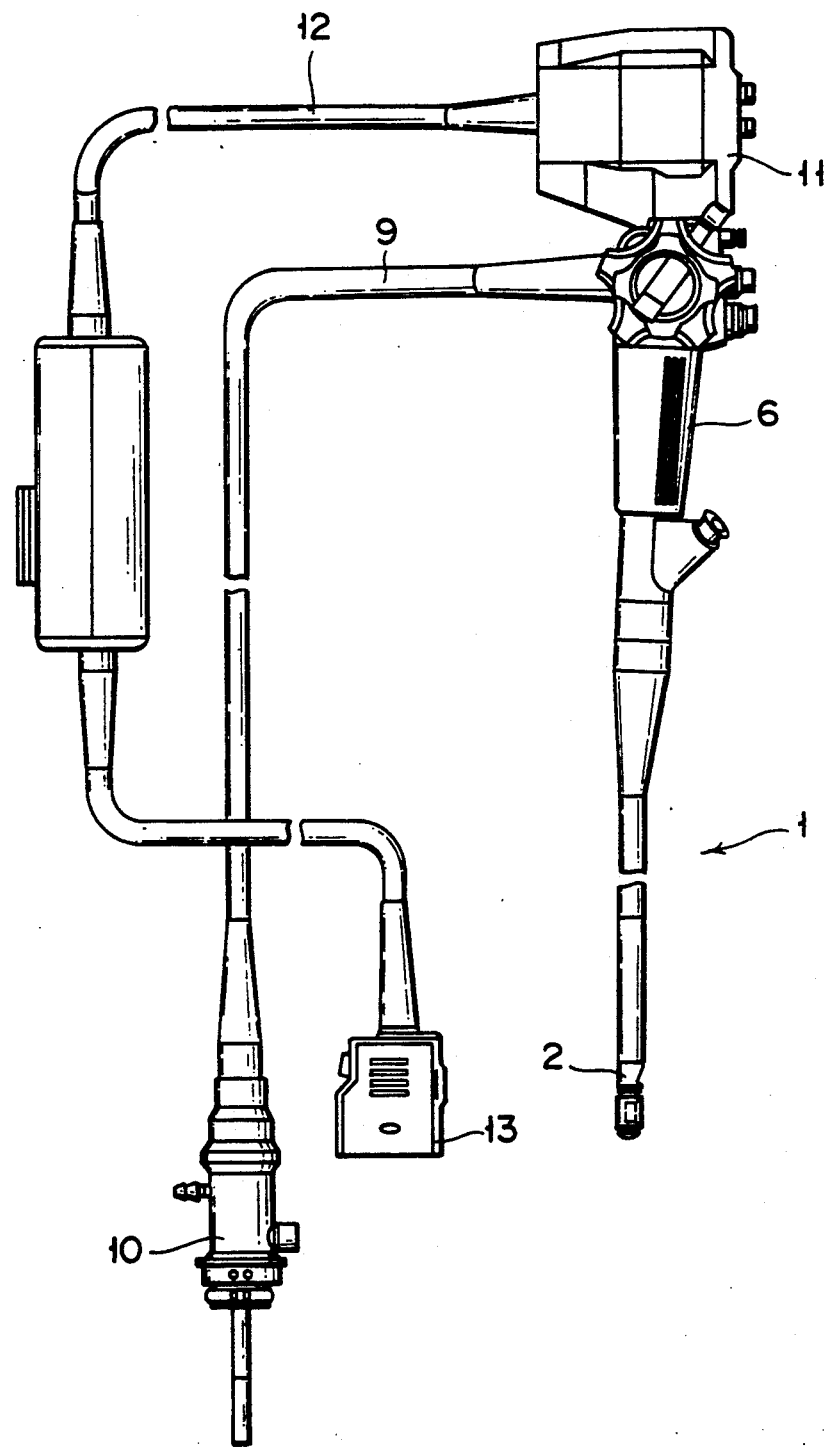
FIG. 19 is a side view of an ultrasonic endoscope according to a fourth modification of the first embodiment.

FIG. 19 shows a fourth modification, in which a solid-state image sensing device (CCD) is contained in distal end portion 2 of insertion section 1 of the ultrasonic endoscope, and auxiliary operating section 11 has no eyepiece portion thereon. The CCD is connected to electric connector 13 by means of a signal cable, and connector 13 is connected to a video processor (not shown) and the ultrasonic observation device (not shown).

Referring now to FIGS. 20 to 29, a second embodiment of the present invention will be described.

FIG. 20 shows an outline of an ultrasonic endoscope according to the second embodiment of the invention. In FIG. 20, numeral 1 denotes an insertion section which comprises flexible portion 4 and bending portion 3. Operating section 6 is connected to the rear end of insertion section 1. Operating section 6 is provided with control knob 7 for controlling bending portion 3, air/water feed buttons 8, and eyepiece portion 14, and is connected with universal cord 9 and electric cable cord 12. First connector 10, which is adapted to be connected to a light source unit (not shown), is attached to the distal end of cord 9, while second connector 13, which is adapted to be connected to an ultrasonic observation unit (not shown), is attached to the distal end of cord 12.

Figure 21:
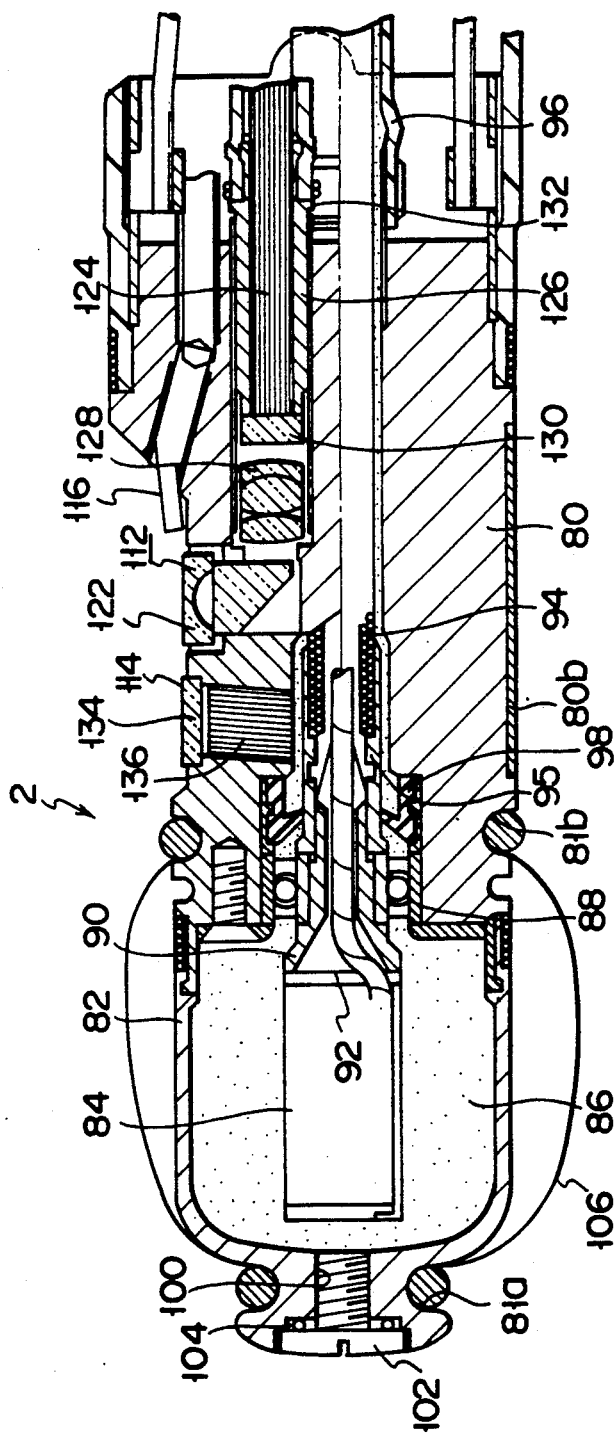
FIG. 21 is a longitudinal sectional view of an insertion section of the ultrasonic endoscope shown in FIG. 20.
Figure 22:
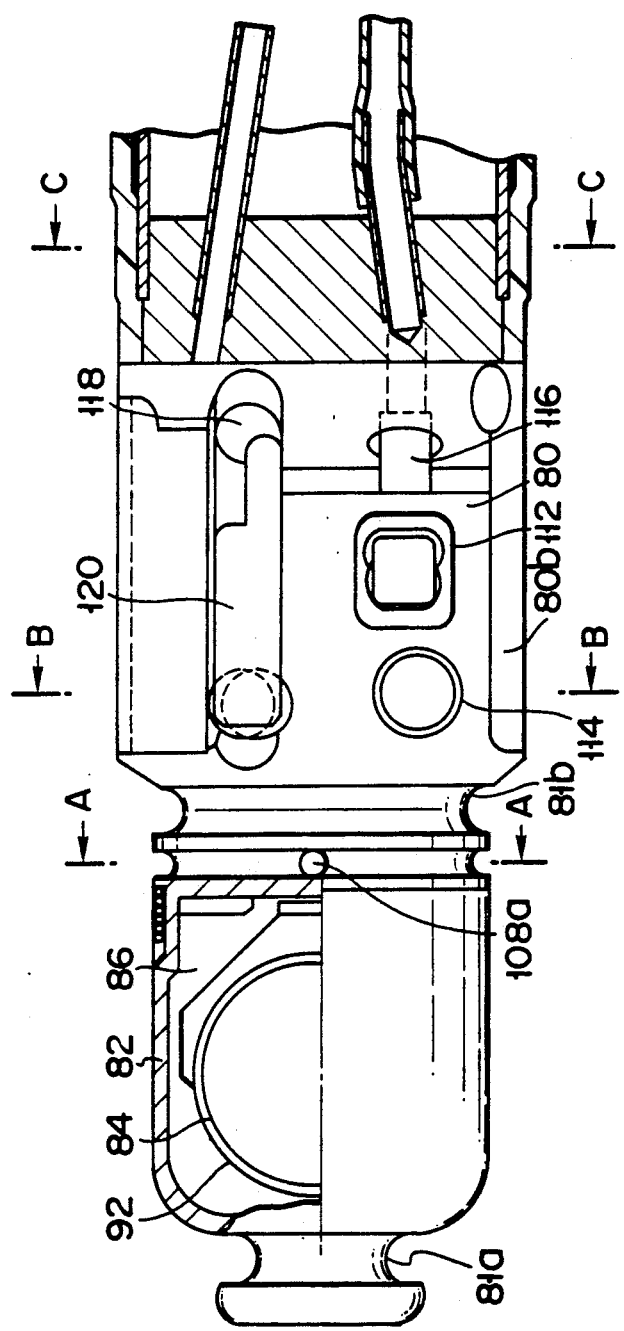
FIG. 22 is a plan view, partially in section, showing the insertion section

FIGS. 21 and 22 show distal end portion 2 of insertion section 1. Distal-end cover 82, formed of a material with high ultrasonic transmission, is attached to the distal end of distal end body 80. Cover 82 contains ultrasonic probe 84 which is used to generate ultrasonic oscillations and detect reflected waves. Also, liquid ultrasonic transmission medium 86 is sealed in cover 82. Probe 84 is bonded to probe holder 90 through the medium of insulating film 92, such as polyimide film. Probe holder 90, which is rotatably supported by means of bearing 88, is connected with hollow flexible drive shaft 94 which is rotated by drive means, such as a motor, in operating section 6. Guide tube 96 is fitted on shaft 94 so as to cover the substantially full length of insertion section 1. The gap between tube 96 and shaft 94, which communicates with the space inside distal end cover 82, is filled with ultrasonic transmission medium 86. Check valve 98 is provided at the junction or connecting portion of probe holder 90 and drive shaft 94. It serves to prevent air bubbles or dust from entering the inside space of cover 82 from the operating section side. Valve 98 is formed of an elastic material, such as rubber, and its distal end is in contact with the outer peripheral surface of junction 95 of drive shaft 94.

Figure 23:
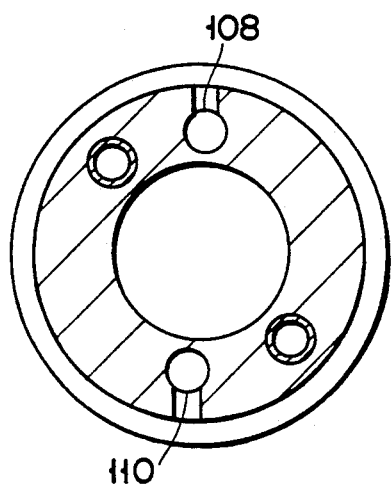
FIG. 23 is a cross-sectional view taken along line A—A of FIG. 22.
Figure 27:
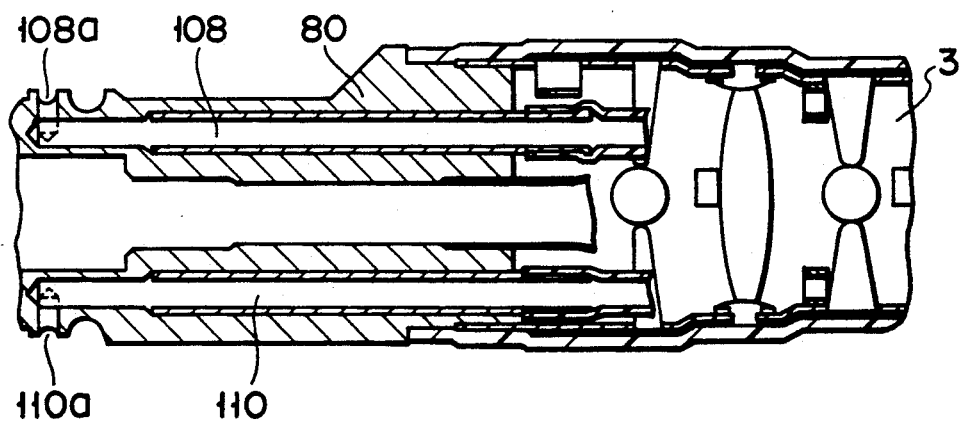
FIG. 27 is a sectional view showing pipes connecting with a balloon.

Formed at the front end of distal end cover 82 is opening 100 through which ultrasonic transmission medium 86 is injected. Opening 100 is sealed by means of screw 102 and O-ring 104. Balloon retaining portions 81a and 81b for retaining both end portions balloons 106 are formed at the front and rear end portions, respectively, of cover 82. As shown in FIGS. 23 and 27, openings 108a and 110a of water supply pipe 108 and drain pipe 110, used to feed and discharge water into and from balloon 106, respectively, are arranged between retaining portions 81a and 81b. As shown in FIG. 27, pipes 108 and 110 are each formed of a pipe member having a relatively thick wall which extends close to the opening, and the tube junction has a suitable wall thickness.

Figure 26:
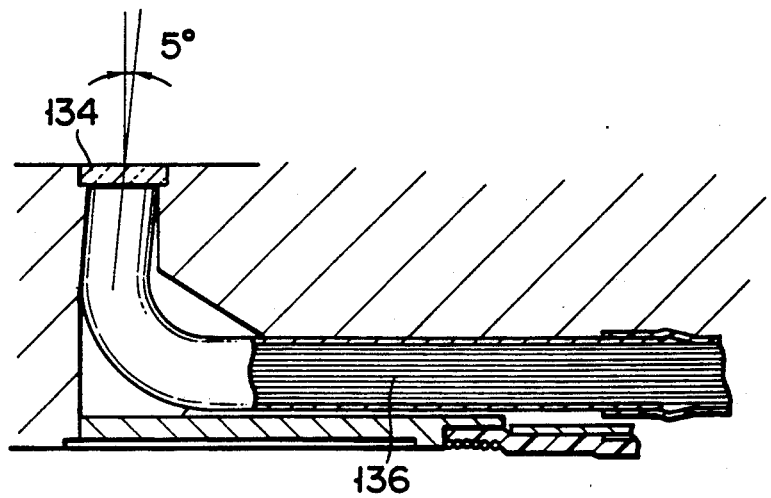
FIG. 26 is a partial sectional view showing an illumination optical system.
Figure 29:
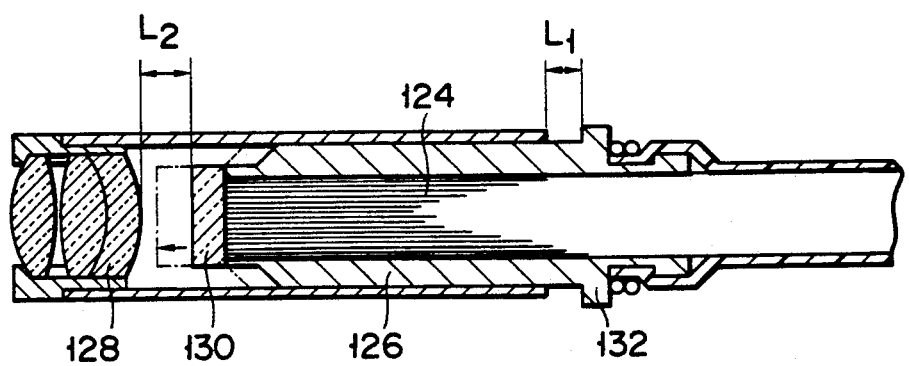
FIG. 29 is a longitudinal sectional view showing an end ferrule of a light guide fiber bundle.

Observation optical system 112, illumination optical system 114, air/water feed nozzle 116, forceps channel 118, and forceps support 120 are arranged on the side portion of distal end body 80. Observation system 112 is composed of objective lens group 122 and image guide fiber bundle 124. As shown in FIG. 29, flange 132 is formed on end ferrule 126 of fiber bundle 124 so that there is a relation L2>L1, in order to prevent dustproof glass 13 from being brought into contact with lens 128 by mistake during focus adjustment. Illumination optical system 114 is composed of illumination lens 134 and light guide fiber bundle 136. As shown in FIG. 26, the direction of illumination of fiber bundle 136 is inclined toward observation optical system 112, at an angle of about 5°, so that an illumination light is directed to the field of view of system 112.

Figure 24:
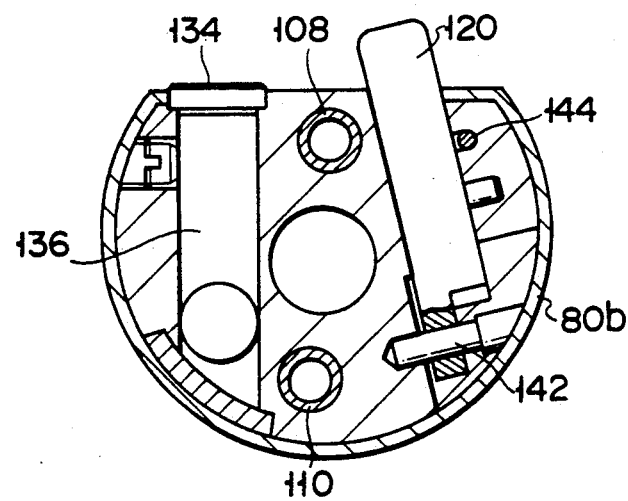
FIG. 24 is a cross-sectional view taken along line B—B of FIG. 22.
Figure 25:
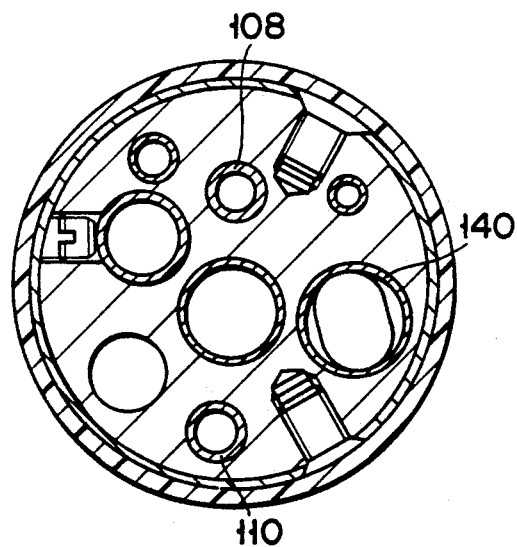
FIG. 25 is a cross-sectional view taken along line A—A of FIG. 22.
Figure 28:
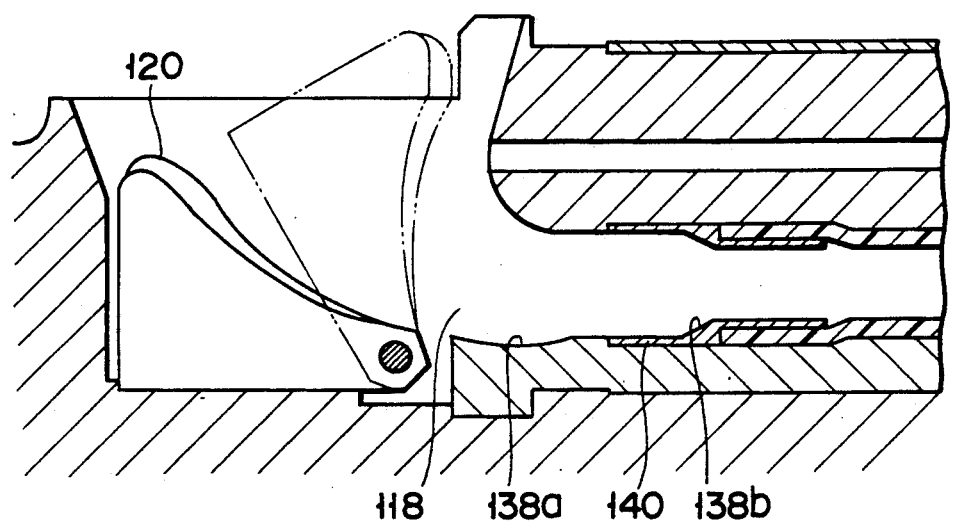
FIG. 28 is a partial sectional view showing the way a forceps support is mounted.

As shown in FIG. 28, forceps channel 118 is provided with slope portions 138a and 138b which allow a medical instrument, such as a forceps, to be smoothly inserted. As shown in FIG. 25, moreover, the cross-sectional shape of channel mouthpiece 140 is in the form of an oval whose major axis is aligned with the rising direction of forceps support 120. Mouthpiece 140 is tapered so that its oval cross section turns circular at its end nearer to the operating section. As shown in FIG. 24, moreover, forceps support 120 is penetrated by shaft 142 which serves as a pivot for the rising motion of support 120. Support 120 can be raised by pulling wire 144 attached thereto.

Cover 80b encloses the whole outer surface of distal end body 80 except those portions at which air/water feed nozzle 116, forceps channel 118, etc. are arranged. Cover 80b, which is formed of an elastic planar member, adheres to distal end body 80 by means of its own elastic force. The gap between cover 80b and distal end body 80 is filled with a filler material, such as silicone, so that there is no play between the two members.

In the ultrasonic endoscope according to the second embodiment, as described above, ring-shaped check valve 98 is disposed at the junction of ultrasonic probe 84 and drive shaft 94, and its distal end is in contact with the outer periphery of drive shaft connecting member 95. Thus, valve 98 can prevent air bubbles or dust from entering the inside space of distal end cover 82 from the operating section side. Accordingly, an ultrasonic beam cannot be scattered or damped by air bubbles or dust from the operating section, so that a satisfactory ultrasonic picture can be obtained.

Figure 30:
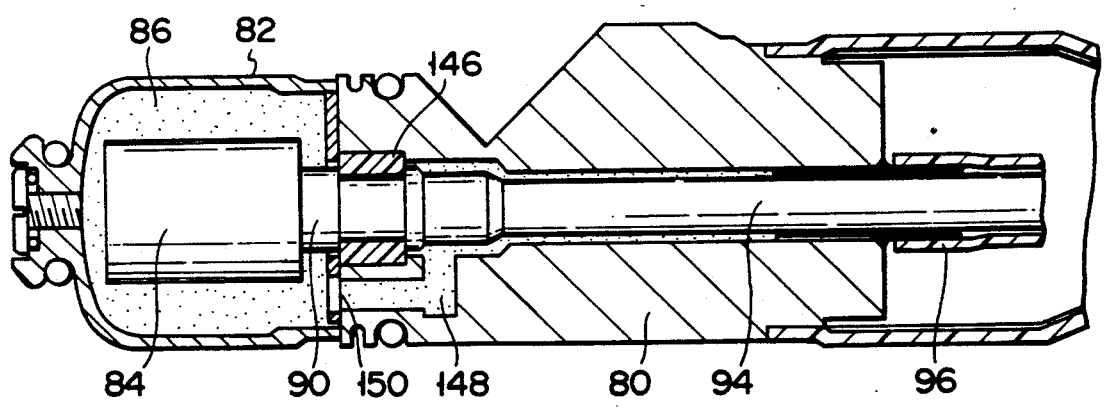
FIG. 30 is a longitudinal sectional view showing a first modification of the insertion section of the endoscope.

FIG. 30 shows a first modification of the ultrasonic endoscope according to the second embodiment. In this first modification, probe holder 90, holding ultrasonic probe 84 therein, is rotatably supported on distal end body 80 by means of slide bearing 146 made of plastic material, such as Teflon or Delrin containing a filler material. Passage 148 is formed by-passing bearing 146 so that ultrasonic transmission medium 86 from the inside of distal end cover 82 can be introduced into guide tube 96 through passage 148. Passage 148 is provided with filter 150, such as a nylon screen, which has a number of pores with a diameter of about 20 to 100μ. Also in this modification, filter 150 has a function to prevent air bubbles or dust from entering the inside space of distal end cover 82 from the operating section side.

Filter paper may be used in place of check valve 98 or filter 150.

Figure 31:
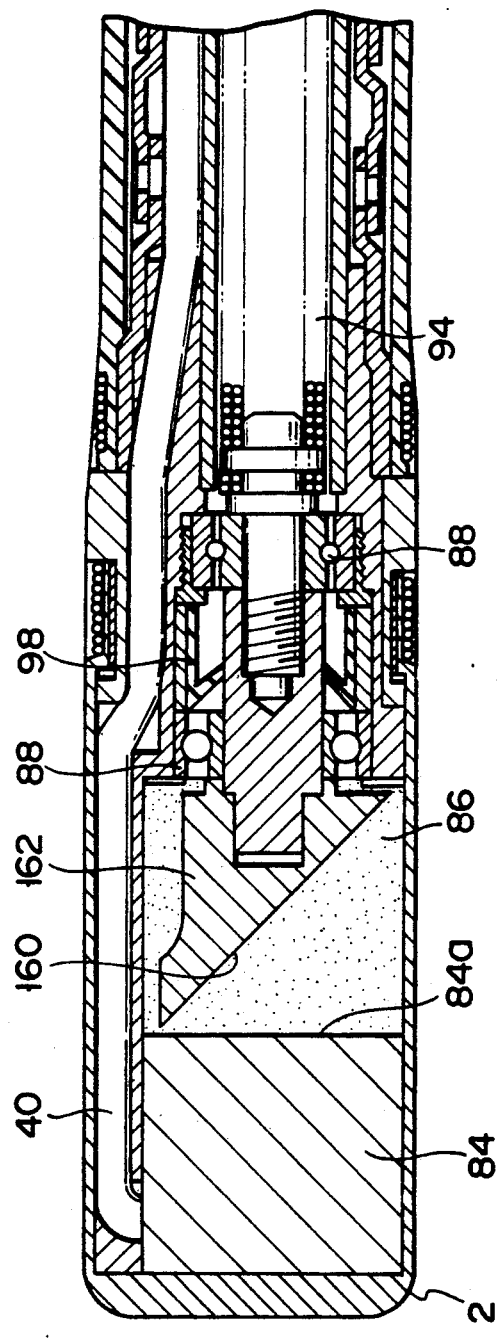
FIG. 31 is a longitudinal sectional view showing a second modification of the insertion section.

FIG. 31 shows a second modification of the ultrasonic endoscope according to the second embodiment. In this second modification, ultrasonic probe 84 is provided with a vibrator which has vibrating surface 84a on its rear face. Acoustic mirror 162 is rockably mounted behind probe 84. Mirror 162 has reflecting surface 160, which faces vibrating surface 84a of probe 84 at an angle of about 45° thereto. The rear portion of acoustic mirror 162 is fixed to flexible drive shaft 94 which extends up to the operating section, so that mirror 162 can be rocked by rocking shaft 94. In this second modification, therefore, an ultrasonic oscillation generated from ultrasonic probe 84 can be scanned at right angles to the axis of insertion section 1 by being reflected by means of reflecting surface 160 of acoustic mirror 162. Also, the oscillation can be scanned over about 360° around the axis of the insertion section by rotating mirror 162.

Check valve 98 of the same construction as the one used in the second embodiment is provided at the junction of acoustic mirror 162 and drive shaft 94, and signal cable 40 is connected to ultrasonic probe 84.

It is to be understood that the present invention is not limited to the embodiments described above, and that various changes and modifications may be effected therein by one skilled in the art without departing from the scope or spirit of the invention.

What is claimed is:

1. An ultrasonic wave endoscope comprising:
   an insertion section having a distal end portion and a proximal end portion, said insertion section having a longitudinal axis;
   ultrasonic transmission and reception means, located in the distal end portion of said insertion section, for generating ultrasonic oscillations and for detecting received reflected waves;
   an operating section connected to the proximal end portion of said insertion section for bending said insertion section, said operation section having a rear end portion; and
   an auxiliary operating section connected to the rear end portion of said operating section on the same longitudinal axis as that of said insertion section, said auxiliary operating section including rotation drive means for rotating said ultrasonic transmission and reception means, wherein said rotation drive means includes:
   a rotary signal transmission unit located in said auxiliary operating section on the same longitudinal axis as that of said insertion section,
   a motor and an encoder arranged in parallel with said rotary signal transmission unit so as to extend through a common plane which is perpendicular to a longitudinal axis of said rotary signal transmission unit, and
   a flexible hollow drive shaft connecting said ultrasonic transmission and reception means and said rotary signal transmission means;
   ultrasonic observation means for observing a signal from said ultrasonic transmission and reception means; and
   a signal cable extending through a hole of said hollow drive shaft, said signal cable having one end connected to said ultrasonic transmission and reception means and another end connected to said rotary signal transmission unit which electrically connects said another end of said signal cable to said ultrasonic observation means;
   said rotary signal transmission unit comprising a multi-level rotator and a through hole communication with said hole of said hollow drive shaft; and
   said signal cable including a first cable having at least one end connected to said ultrasonic transmission and reception means, and a second cable having at least one end connected to said multi-level rotator, at least one other end of said first cable being connected to at least one other end of said second cable at a rear end portion of said rotary signal transmission unit.

2. An ultrasonic endoscope, comprising:
   an insertion section having a distal end portion and a proximal end portion;
   ultrasonic transmission and reception means, located in the distal end portion of said insertion section, for generating ultrasonic oscillations and for detecting reflected waves;
   rotation drive means for rotating said ultrasonic transmission and reception means;

a drive shaft connecting said ultrasonic transmission and reception means to said rotation drive means;

a cover enclosing said ultrasonic transmission and reception means;

a guide tube enclosing said drive shaft;

an ultrasonic transmission medium sealed inside said cover and in a space between said drive shaft and said guide tube;

a passage for said ultrasonic transmission medium, said passage communication with the inside of said cover and said space, and surrounding a connecting portion of said ultrasonic transmission and reception means and said drive shaft; and trap means, comprising a check valve, provided in said passage, for preventing air bubbles or dust from entering the inside of said cover from the inside of said guide tube.

3. The ultrasonic endoscope of claim 2, wherein said ultrasonic transmission and reception means includes:

an ultrasonic vibrator disposed at the distal end portion of said insertion section; and an acoustic mirror disposed behind said ultrasonic vibrator and fixed to said drive shaft.

4. An ultrasonic endoscope, comprising:

an insertion section having a distal end portion and a proximal end portion;

ultrasonic transmission and reception means, located in the distal end portion of said insertion section, for generating ultrasonic oscillations and for detecting reflected waves;

rotation drive means for rotating said ultrasonic transmission and reception means;

a drive shaft connecting said ultrasonic transmission and reception means to said rotation drive means;

a cover enclosing said ultrasonic transmission and reception means;

a guide tube enclosing said drive shaft;

an ultrasonic transmission medium sealed inside said cover and in a space between said drive shaft and said guide tube;

a passage for said ultrasonic transmission medium, said passage communicating with the inside of said cover and said space, and surrounding a connecting portion of said ultrasonic transmission and reception means and said drive shaft; and trap means, comprising a filter, provided in said passage, for preventing air bubbles or dust from entering the inside of said cover from the inside of said guide tube.

5. The ultrasonic endoscope of claim 4, wherein said ultrasonic transmission and reception means includes:

an ultrasonic vibrator disposed at the distal end portion of said insertion section; and an acoustic mirror disposed behind said ultrasonic vibrator and fixed to said drive shaft.

* * * * *